US012670980B2

(12) United States Patent
Tang et al.

(10) Patent No.: US 12,670,980 B2
(45) Date of Patent: Jun. 30, 2026

(54) PROCESSING METHOD AND DEVICE OF HEMATOMA ASPIRATION DECISION-MAKING SYSTEM FOR INTRACEREBRAL HEMORRHAGE

(71) Applicant: Tongji Hospital, Tongji Medical College, Huazhong University of Science and Technology, Wuhan (CN)

(72) Inventors: Zhouping Tang, Wuhan (CN); Jian Shi, Wuhan (CN); Danyang Chen, Wuhan (CN); Wenjie Liu, Wuhan (CN); Bo Tao, Wuhan (CN); Xingwei Zhao, Wuhan (CN); Chao Pan, Wuhan (CN); Ping Zhang, Wuhan (CN); Qing Ye, Wuhan (CN); Cai Meng, Wuhan (CN); Diansheng Chen, Wuhan (CN)

(73) Assignee: Tongji Hospital, Tongji Medical College, Huazhong University of Science and Technology, Wuhan (CN)

( * ) Notice: Subject to any disclaimer, the term of this patent is extended or adjusted under 35 U.S.C. 154(b) by 0 days.

(21) Appl. No.: 19/204,941

(22) Filed: May 12, 2025

(65) Prior Publication Data

US 2026/0128153 A1 May 7, 2026

(30) Foreign Application Priority Data

Nov. 6, 2024 (CN) .......................... 202411570263.6

(51) Int. Cl.
| | |
|---|---|
| *G16H 20/40* | (2018.01) |
| *G16H 10/60* | (2018.01) |
| *G16H 20/17* | (2018.01) |

(52) U.S. Cl.
CPC ............. *G16H 20/40* (2018.01); *G16H 10/60* (2018.01); *G16H 20/17* (2018.01)

(58) Field of Classification Search
CPC .. G06N 3/02; G06N 5/02; G06N 3/08; G16H 50/70
USPC ......................................................... 705/2, 3
See application file for complete search history.

(56) References Cited

U.S. PATENT DOCUMENTS

| | | | | |
|---|---|---|---|---|
| 11,961,619 B1 * | 4/2024 | LaBorde | .................. | G06N 3/02 |
| 2019/0012783 A1 * | 1/2019 | Zahid | ..................... | A61B 6/032 |

FOREIGN PATENT DOCUMENTS

| | | | | | |
|---|---|---|---|---|---|
| CN | 114129240 | B | * 11/2022 | ............. | A61B 34/10 |
| CN | 117789992 | A | 3/2024 | | |
| CN | 118486435 | A | * 8/2024 | ............... | G06N 3/08 |
| CN | 118824577 | A | * 10/2024 | ............... | G06N 5/02 |

(Continued)

*Primary Examiner* — Dilek B Cobanoglu
(74) *Attorney, Agent, or Firm* — Nitin Kaushik

(57) ABSTRACT

The present application provides a processing method and device of a hematoma aspiration decision-making system for intracerebral hemorrhage. A two-layer deep neural network is constructed for processing of a hematoma aspiration protocol, and a perception-decision-making-control method based on a time series is thus realized, which overcomes unpredictability of results of hematoma aspiration processes existing in the prior art, provides direct and convenient information transmission for surgeons to make decisions, can effectively improve the accuracy of aspiration treatment protocols for intracerebral hematoma, and provides digital, intelligent, and powerful support for clinical hematoma aspiration treatments.

8 Claims, 5 Drawing Sheets

(56)          References Cited

FOREIGN PATENT DOCUMENTS

| | | | |
|---|---|---|---|
| KR | 20230109885 A | 7/2023 | |
| WO | WO-2023068049 A1 * | 4/2023 | ............ G16H 50/70 |
| WO | WO2023241012 A1 | 12/2023 | |
| WO | WO-2024192175 A1 * | 9/2024 | ............ G16H 30/40 |

* cited by examiner

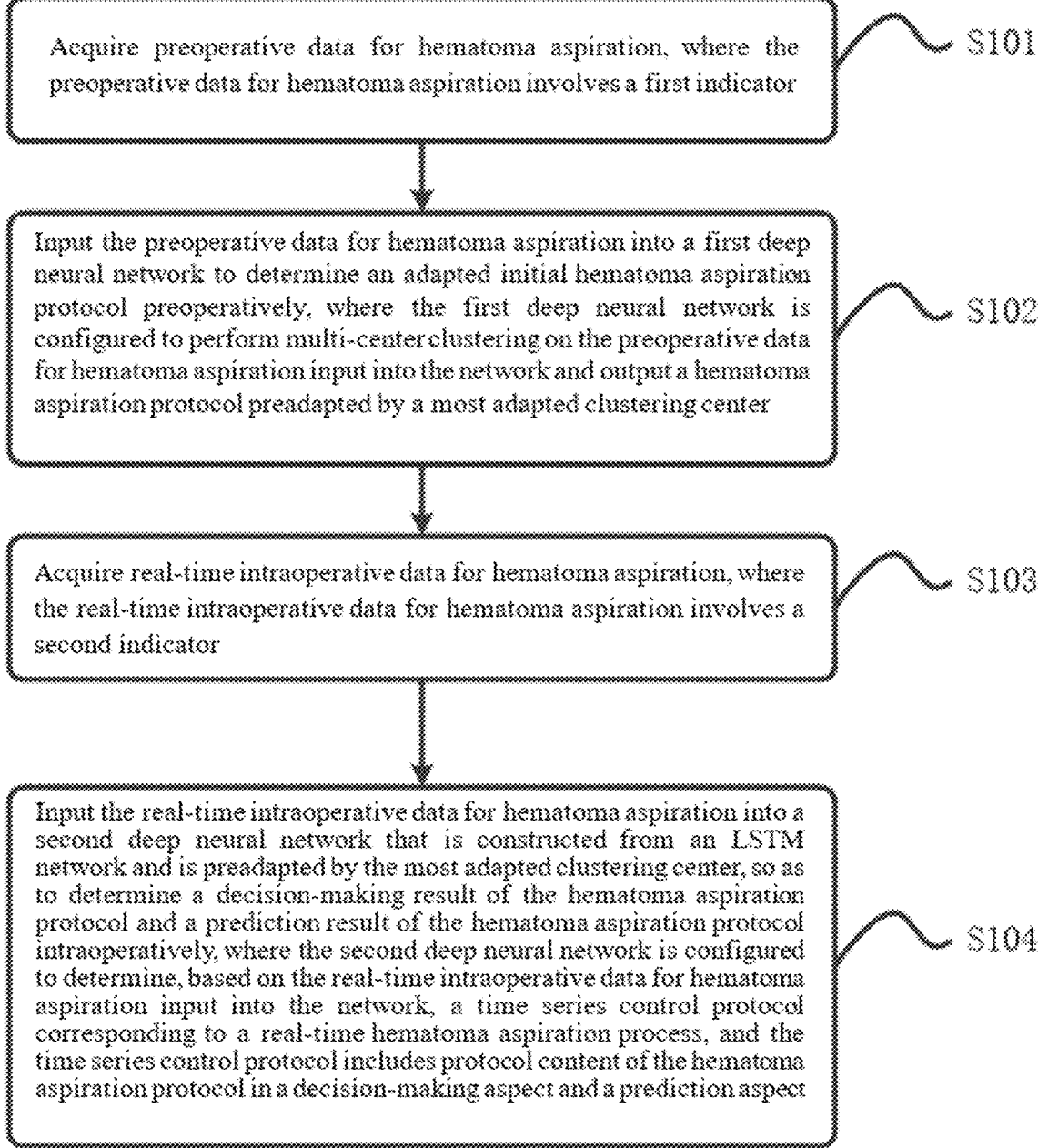

Acquire preoperative data for hematoma aspiration, where the preoperative data for hematoma aspiration involves a first indicator — S101

Input the preoperative data for hematoma aspiration into a first deep neural network to determine an adapted initial hematoma aspiration protocol preoperatively, where the first deep neural network is configured to perform multi-center clustering on the preoperative data for hematoma aspiration input into the network and output a hematoma aspiration protocol preadapted by a most adapted clustering center — S102

Acquire real-time intraoperative data for hematoma aspiration, where the real-time intraoperative data for hematoma aspiration involves a second indicator — S103

Input the real-time intraoperative data for hematoma aspiration into a second deep neural network that is constructed from an LSTM network and is preadapted by the most adapted clustering center, so as to determine a decision-making result of the hematoma aspiration protocol and a prediction result of the hematoma aspiration protocol intraoperatively, where the second deep neural network is configured to determine, based on the real-time intraoperative data for hematoma aspiration input into the network, a time series control protocol corresponding to a real-time hematoma aspiration process, and the time series control protocol includes protocol content of the hematoma aspiration protocol in a decision-making aspect and a prediction aspect — S104

FIG. 1

PROCESSING METHOD AND DEVICE OF HEMATOMA ASPIRATION DECISION-MAKING SYSTEM FOR INTRACEREBRAL HEMORRHAGE

CROSS-REFERENCE TO RELATED APPLICATIONS

The application claims priority to Chinese patent application No. 2024115702636, filed on Nov. 6, 2024, the entire contents of which are incorporated herein by reference.

TECHNICAL FIELD

The present application relates to the field of medical technologies, and in particular, to a processing method and device of a hematoma aspiration decision-making system for intracerebral hemorrhage.

BACKGROUND

Minimally invasive surgery is a new method for surgical treatments of intracerebral hemorrhage, offering certain advantages such as minimal trauma and high hematoma clearance rate. Among minimally invasive surgical treatments, the most important method is hematoma aspiration. Hematoma aspiration can be understood as a process involving: drilling through a skull, and then placing a drainage tube to perform operations such as liquefaction, aspiration, and drainage on a hematoma, so as to reduce the hematoma and lower intracranial pressure.

In current clinical treatments, the hematoma aspiration method mainly relies on experience of clinicians. First, a surgeon determines an aspiration protocol based on preoperative signs and indicators of a patient such as an age, a hematoma site, a hematoma size, and preoperative images; and during an aspiration process, the surgeon relies on experience to control an aspiration velocity, ultimately achieving the purpose of reducing hematoma and lowering intracranial pressure.

However, the hematoma aspiration method undergoes a long operation time, and the control of the aspiration process is entirely dependent on personal experience of the surgeon. During a long period of surgery, the aspiration effect cannot be guaranteed, and the following problems may easily occur: (1) incomplete aspiration: during the hematoma aspiration process, the hematoma is deformed due to aspiration, and residual hematoma fails to be absorbed, resulting in deterioration of intracerebral hemorrhage condition; (2) over-aspiration: as changes of the hematoma cannot be predicted during the aspiration process, over-aspiration may occur, which causes damages to normal brain tissue and affect normal brain functions; and (3) unstable control of the aspiration process: the aspiration process causes acute fluctuations in intracranial pressure, which affects the pressure balance and potentially causes vascular rupture, etc., leading to a secondary damage to the brain tissue.

In view of this, there exists a demand for applying digital technologies to assist hematoma aspiration. The inventors of the present application found that by adopting existing solutions, only part of functions can be implemented, but for example, real-time monitoring of key information during hematoma aspiration is neglected, treatment protocols are merely recommended based on preoperative information, and digital control and intelligent real-time decision-making cannot be achieved during the hematoma aspiration process. For another example, the existing solutions only focus on real-time situations during the hematoma aspiration process and lack real-time prediction, making it difficult to control impending abnormalities.

That is to say, the prior art is still in a relatively primitive stage for how to assist hematoma aspiration based on the digital technologies, fails to reach a deep level of intelligent processing effect, and still lacks practical value.

SUMMARY

The present application provides a processing method and device of a hematoma aspiration decision-making system for intracerebral hemorrhage. A two-layer deep neural network is constructed for processing of a hematoma aspiration protocol, and a perception-decision-making-control method based on a time series is thus realized, which overcomes unpredictability of results of hematoma aspiration processes existing in the prior art, provides direct and convenient information transmission for surgeons to make decisions, can effectively improve the accuracy of aspiration treatment protocols for intracerebral hematoma, and provides digital, intelligent, and powerful support for clinical hematoma aspiration treatments.

In a first aspect, the present application provides a processing method of a hematoma aspiration decision-making system for intracerebral hemorrhage. The method includes:

acquiring preoperative data for hematoma aspiration, where the preoperative data for hematoma aspiration involves a first indicator;

inputting the preoperative data for hematoma aspiration into a first deep neural network to determine an adapted initial hematoma aspiration protocol preoperatively, where the first deep neural network is configured to perform multi-center clustering on the preoperative data for hematoma aspiration input into the network and output a hematoma aspiration protocol preadapted by a most adapted clustering center;

acquiring real-time intraoperative data for hematoma aspiration, where the real-time intraoperative data for hematoma aspiration involves a second indicator;

inputting the real-time intraoperative data for hematoma aspiration into a second deep neural network that is constructed from an LSTM network and is preadapted by the most adapted clustering center, so as to determine a decision-making result of the hematoma aspiration protocol and a prediction result of the hematoma aspiration protocol intraoperatively, where the second deep neural network is configured to determine, based on the real-time intraoperative data for hematoma aspiration input into the network, a time series control protocol corresponding to a real-time hematoma aspiration process, and the time series control protocol includes protocol content of the hematoma aspiration protocol in a decision-making aspect and a prediction aspect.

In a second aspect, the present application provides a processing device of a hematoma aspiration decision-making system for intracerebral hemorrhage. The device includes:

a first acquisition unit, configured to acquire preoperative data for hematoma aspiration, where the preoperative data for hematoma aspiration involves a first indicator;

a first processing unit, configured to input the preoperative data for hematoma aspiration into a first deep neural network to determine an adapted initial hematoma aspiration protocol preoperatively, where the first deep neural network is configured to perform multi-center clustering on the preoperative data for hematoma aspiration input into the network and output a hematoma aspiration protocol preadapted by a most adapted clustering center;

a second acquisition unit, configured to acquire real-time intraoperative data for hematoma aspiration, where the real-time intraoperative data for hematoma aspiration involves a second indicator;

a second processing unit, configured to input the real-time intraoperative data for hematoma aspiration into a second deep neural network that is constructed from an LSTM network and is preadapted by the most adapted clustering center, so as to determine a decision-making result of the hematoma aspiration protocol and a prediction result of the hematoma aspiration protocol intraoperatively, where the second deep neural network is configured to determine, based on the real-time intraoperative data for hematoma aspiration input into the network, a time series control protocol corresponding to a real-time hematoma aspiration process, and the time series control protocol includes protocol content of the hematoma aspiration protocol in a decision-making aspect and a prediction aspect.

In a third aspect, the present application provides a hematoma aspiration decision-making system. The system includes a processor and a memory, where the memory has a computer program stored therein, and the processor, when calling the computer program in the memory, executes the method provided by the first aspect of the present application or provided by any of possible implementations of the first aspect of the present application.

In a fourth aspect, the present application provides a computer-readable storage medium. The computer-readable storage medium stores a plurality of instructions, and the instructions are suitable for being loaded by a processor to execute the method provided by the first aspect of the present application or provided by any of possible implementations of the first aspect of the present application.

It can be seen from the above content that the present application has the following beneficial effects:

According to the present application, aiming at a goal of assisting hematoma aspiration treatments, a two-layer deep neural network is constructed for processing of a hematoma aspiration protocol, and a perception-decision-making-control method based on a time series is thus realized, which overcomes unpredictability of results of hematoma aspiration processes existing in the prior art, provides direct and convenient information transmission for surgeons to make decisions, can effectively improve the accuracy of intracerebral hematoma aspiration treatment protocols, and provides digital, intelligent, and powerful support for clinical hematoma aspiration treatments.

BRIEF DESCRIPTION OF THE DRAWINGS

To describe the technical solutions in the embodiments of the present application more clearly, the accompanying drawings required to describe the merely embodiments are briefly described below. Apparently, the accompanying drawings described below are only some embodiments of the present application. Those skilled in the art may further obtain other accompanying drawings based on these accompanying drawings without creative efforts.

FIG. 1 is a flow diagram of a processing method of a hematoma aspiration decision-making system for intracerebral hemorrhage according to the present application;

DETAILED DESCRIPTION OF THE EMBODIMENTS

Figure 2:
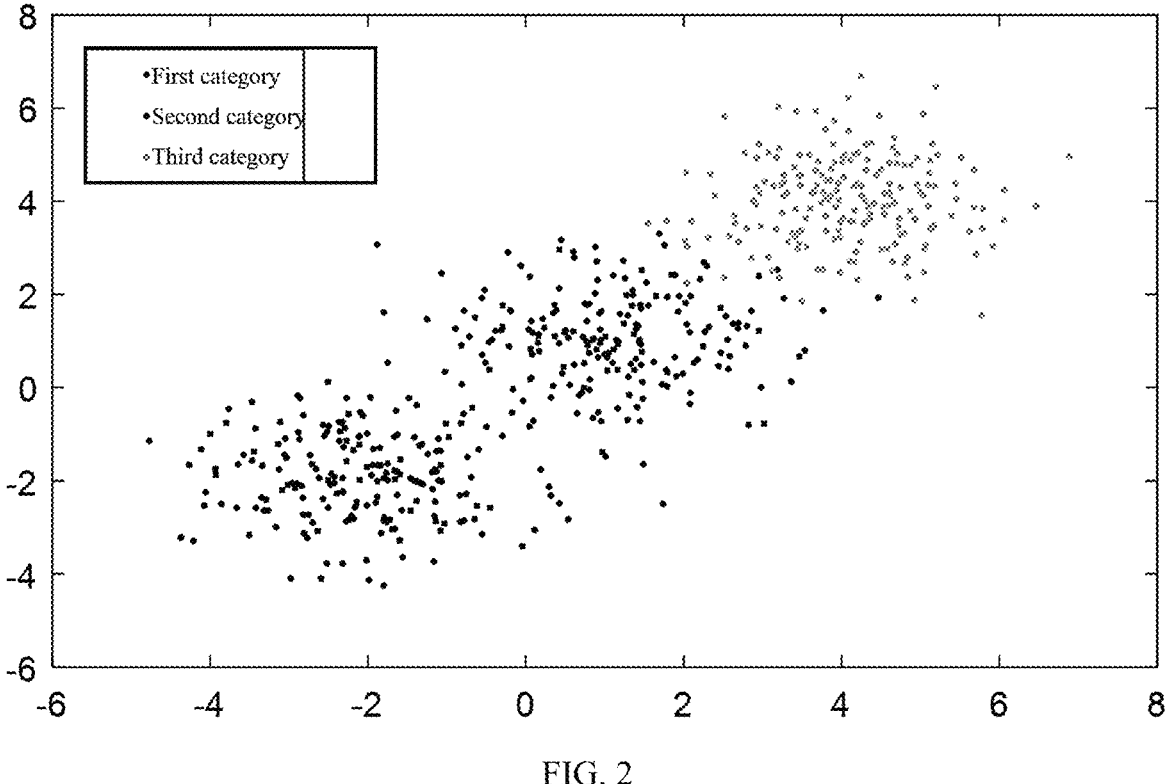
FIG. 2 is a scenario diagram of clustering processing according to the present application.

The following clearly and completely describes the technical solutions in the embodiments of the present application with reference to the accompanying drawings in the embodiments of the present application. Apparently, the described embodiments are merely some but not all of the embodiments of the present application. All other embodiments obtained by those skilled in the art based on the embodiments of the present application without creative efforts shall fall within the protection scope of the present application.

The terms "first", "second", and so on in the description and claims of the present application and in the above accompanying drawings are intended to distinguish between similar objects but do not necessarily indicate a specific order or sequence. It should be understood that data used in such a way may be exchanged under proper conditions to make it possible to implement the embodiments described here in other sequences apart from those illustrated or described here. Moreover, the terms "include", "comprise", and any other variants mean to cover the non-exclusive inclusion, for example, a process, method, system, product, or device that includes a list of steps or modules is not necessarily limited to those steps or modules which are clearly listed, but may include other steps or units which are not expressly listed or inherent to such a process, method, system, product, or device. The names or numbers of steps in the present application do not mean that the steps in the method flow must be executed in a time/logical sequence indicated by the names or numbers, and the execution order of the named or numbered process steps can be changed according to the technical purpose to be achieved, as long as the same or similar technical effects can be achieved.

The division of modules appearing in the present application is based on logic, and there may be other division methods when the division is realized in actual application. For example, a plurality of modules can be incorporated or integrated into another system, or some features can be ignored or are not executed; furthermore, the mutual coupling or direct coupling or communication connection shown or discussed can be realized through certain interfaces, and the indirect coupling or communication connection between the modules can be electrical or other similar forms, which are not limited in the present application. Also, the modules or submodules mentioned above as separate components can be, or may not be physically separated, or may not be physical modules, or can be distributed across a plurality of circuit modules; and some or all of the modules can be selected according to actual needs to achieve the purpose of the solution of the present application.

Before describing a processing method of a hematoma aspiration decision-making system for intracerebral hemorrhage provided by the present application, the background content involved in the present application is first described.

The present application provides a processing method and device of a hematoma aspiration decision-making system for intracerebral hemorrhage, and a computer-readable storage medium, which can be applied to the hematoma aspiration decision-making system. According to the present application, a two-layer deep neural network is constructed for processing of a hematoma aspiration protocol, and a perception-decision-making-control method based on a time series is thus realized, which overcomes unpredictability of results of hematoma aspiration processes existing in the prior art, provides direct and convenient information transmission for surgeons to make decisions, can effectively improve the accuracy of intracerebral hematoma aspiration treatment protocols, and provides digital, intelligent, and powerful support for clinical hematoma aspiration treatments.

For the processing method of a hematoma aspiration decision-making system for intracerebral hemorrhage referred to in the present application, an executing body may be a processing device of a hematoma aspiration decision-making system for intracerebral hemorrhage, or a different type of hematoma aspiration decision-making system such as a server, a physical host, or user equipment (UE) that integrates the processing device of a hematoma aspiration decision-making system for intracerebral hemorrhage. Among them, the processing device of a hematoma aspiration decision-making system for intracerebral hemorrhage may be implemented by means of hardware or software; the UE may specifically be terminal equipment such as a smartphone, a tablet computer, a laptop, a desktop computer, or a personal digital assistant (PDA); and the hematoma aspiration decision-making system may be set up by means of a cluster of equipment.

It can be understood that the hematoma aspiration decision-making system executing the processing method of a hematoma aspiration decision-making system for intracerebral hemorrhage according to the present application, or the hematoma aspiration decision-making system equipped with application services corresponding to the processing method of a hematoma aspiration decision-making system for intracerebral hemorrhage according to the present application, can be deployed in clinical application scenarios, either on equipment specifically responsible for assisting hematoma aspiration treatments, or on equipment responsible for other work (such as other clinical treatments or even routine office work) in addition to assisting hematoma aspiration treatments, which obviously achieves higher flexibility. Moreover, the hematoma aspiration system may be either on-site equipment or equipment that provides remote services to the site through web or other types of remote services. This may also occur in actual situations. Therefore, specific equipment types and equipment deployment forms of the hematoma aspiration decision-making system can be flexibly adjusted with actual needs, and will not be specifically limited in the present application.

Next, the processing method of a hematoma aspiration decision-making system for intracerebral hemorrhage provided by the present application is to be introduced.

First, referring to FIG. 1, which illustrates a flow diagram of a processing method of a hematoma aspiration decision-making system for intracerebral hemorrhage according to the present application. The processing method of a hematoma aspiration decision-making system for intracerebral hemorrhage provided by the present application may specifically include the following steps S101 to S104:

S101, acquiring preoperative data for hematoma aspiration, where the preoperative data for hematoma aspiration involves a first indicator.

It can be understood that according to the present application, data support for hematoma aspiration decision-making involves both preoperative and intraoperative phases. In this regard, in both the preoperative and intraoperative phases, data is collected in accordance with corresponding indicators, facilitating the two-layer deep neural network to provide a processing basis for processing of the hematoma aspiration protocol.

For ease of illustration, data acquired preoperatively is denoted as preoperative data for hematoma aspiration, which involves a first indicator and corresponds to a first deep neural network; and data acquired in real time intraoperatively is denoted as real-time intraoperative data for hematoma aspiration, which involves a second indicator and corresponds to a second deep neural network.

As an exemplary embodiment herein, the first indicator involved in the preoperative data for hematoma aspiration may specifically include:

an age, an NIHSS score (a common clinical stroke scale that quantifies severity by rating), a medical history, blood pressure, blood oxygen, a heart rate, intracranial pressure, a hematoma location, a hematoma volume, a CT image and an MRI image (both may be referred to as preoperative images), and other indicators.

It can be understood that this provides a specific implementation for the content of the preoperative data for hematoma aspiration.

Generally, the acquisition of the preoperative data for hematoma aspiration in step S101 refers to acquisition of readily available data. For example, the data can be directly retrieved from relevant systems, can also be manually input, and certainly has the possibility of being collected in real time. However, this means that hardware and software of the system need to be modified. Considering that these data are common clinical data, specific modes of data collection and corresponding data collection equipment/devices involved will not be elaborated herein.

After the preoperative data for hematoma aspiration is acquired, preprocessing can also be involved. For example, data of multiple modalities can be digitized by using digitization methods, and then digitized features can be unified under the same metric by using normalization or standardization methods, so as to form data that is more convenient for models to process. In specific operations, preprocessing can be carried out by corresponding automated processing tools or even AI products such as deep neural networks, which is more flexible as long as the goal of data preprocessing can be achieved.

It should be noted that the acquisition of the preoperative data for hematoma aspiration in step S101 may also directly involve the preprocessing mentioned above, which is also possible in actual situations.

S102, inputting the preoperative data for hematoma aspiration into a first deep neural network to determine an adapted initial hematoma aspiration protocol preoperatively, where the first deep neural network is configured to perform multi-center clustering on the preoperative data for hematoma aspiration input into the network and output a hematoma aspiration protocol preadapted by a most adapted clustering center.

Referring to FIG. 2 which illustrates a scenario diagram of clustering processing according to the present application, it can be understood that according to the present application, a hematoma aspiration protocol adapted to a current patient (user) is determined based on the acquired preoperative data for hematoma aspiration prior to a hematoma aspiration surgery.

Specifically, multi-center clustering is carried out through a first deep neural network during this process. It can be understood that according to the present application, an adapted hematoma aspiration protocol is preset for different clustering centers (clustering clusters), so that after the clustering processing, i.e., the multi-center clustering is completed, the most adapted clustering center (the most adapted clustering center determined based on a minimal distance principle) for current situations of the patient can be determined, and a hematoma aspiration protocol preadapted by the most adapted clustering center is an initial hematoma aspiration protocol that can be output by the network. The initial hematoma aspiration protocol is also the hematoma aspiration protocol determined by digital and intelligent means in the preoperative phase, and subsequent decision-making and prediction of a hematoma aspiration protocol in the intraoperative phase is carried out based on the initial hematoma aspiration protocol.

The first deep neural network mainly aims to implement multi-center clustering processing, and a model architecture specifically used thereby is obviously flexible and can be configured according to actual situations. The model architecture, for example, can adopt an existing model architecture, or, for example, can be optimized and improved based on the existing model architecture, or, for example, can adopt a model architecture that is fully self-developed and more novel.

For different clustering centers (clustering clusters) involved in the clustering process, it can be understood that according to the present application, these different clustering centers are preconfigured based on different configured sample data (including real patient data, data modified based on the real patient data, and virtual patient data that is directly configured) and corresponding to clustering processing that may be involved subsequently. After different clustering centers are determined, corresponding and adapted hematoma aspiration protocols can be configured one by one. Therefore, by carrying out clustering processing through the model subsequently, the initial hematoma aspiration protocol preadapted by the clustering center that is most adapted to the clustering processing can be obtained.

As an instance, the present application can include the following preprocessing:

(1) acquiring an existing case set and denoting as D={$x_1$, $x_2$, . . . , $x_n$}, where $x_i$ represents a single case;

(2) randomly selecting k points {$n_1$, $n_2$, . . . , $n_k$} from D as starting points;

(3) calculating distances from all points {$x_1$, $x_2$, . . . , $x_n$} to {$n_1$, $n_2$, . . . , $n_k$}, and calculating a distance function using Euclidean distances, where a calculation formula of corresponding Euclidean distances is as follows:

$$d_{ij} = \|x_i - n_j\|_2,$$

finally, a distance matrix of the points is obtained:

$$\begin{bmatrix} d_{11} & d_{12} & \cdots & d_{1k} \\ d_{21} & d_{22} & & \\ \vdots & & \ddots & \vdots \\ d_{n1} & & \cdots & d_{nk} \end{bmatrix};$$

(4) classifying each point {$x_1$, $x_2$, . . . , $x_n$} into a category of nearest center points, obtaining k categories of point clusters, and recalculating center points of the point clusters using the Euclidean distance again;

(5) repeating (3) and (4) until the center points of the point clusters no longer change, and taking centers of final multiple point clusters as respective center points of the k categories; and (6) finally, classifying k categories $C_1$, $C_2$, . . . , $C_k$ based on the point cluster centers {$c_1$, $C_2$, . . . , $c_k$} that are finally obtained, where these categories are classifications of patient characteristics, commonly known as patient categories.

Since a corresponding and adapted hematoma aspiration protocol (protocol template) is configured for each predetermined category, after the hematoma aspiration protocol is put into practical use, when new patient data x is input, a distance $d_1$, $d_2$, . . . , $d_k$ between x and the point cluster center {$c_1$, $c_2$, . . . , $c_k$} is calculated, the center point c with the minimal distance is selected as the center category (clustering center) of x, and thus the patient category and a corresponding initial hematoma aspiration protocol can be determined, thereby obtaining an initial treatment protocol and completing initial decision-making.

Specifically, as an exemplary embodiment herein, the protocol content of the initial hematoma aspiration protocol may include:

a tolerance range of changes in intracranial pressure, a single aspiration duration, a hematoma state, whether other drug injections (including a hematoma liquefier, etc.) are needed, and a maximum aspiration velocity, etc.

S103, acquiring real-time intraoperative data for hematoma aspiration, where the real-time intraoperative data for hematoma aspiration involves a second indicator.

It can be understood that after the initial hematoma aspiration protocol is obtained, a corresponding hematoma aspiration treatment can be carried out. During a hematoma aspiration treatment process, or intraoperatively, the decision-making and prediction of the present application for the hematoma aspiration protocol can be continuously carried out in real time, so as to accurately control the hematoma aspiration protocol in real time.

In this regard, real-time intraoperative data for hematoma aspiration corresponding to the second indicator needs to be acquired in real time in the intraoperative phase, so as to provide a reference basis for subsequent processing by the second deep neural network.

As an exemplary embodiment herein, the second indicator involved in the intraoperative data for hematoma aspiration may specifically include:

an aspiration velocity, a fluid inlet velocity, blood pressure, blood oxygen, a heart rate, intracranial pressure, a hematoma location, and a hematoma size, etc.

The aspiration velocity and the fluid inlet velocity can be measured by a micro flowmeter, and the micro flowmeter is used to directly detect a flow rate of fluid in a fluid inlet and outlet channel. Increase and decrease of mass per unit time is calculated by a gravimeter, for correcting flow of fluid inlet and outlet, and the final flow can be represented by the following formulas:

$$v_{in} = \frac{1}{2}\left(v_1 + \frac{\Delta m_1}{\rho_1 t}\right),$$

9

-continued $$v_{out} = \frac{1}{2}\left(v_2 + \frac{\Delta m_2}{\rho_2 t}\right),$$

where $v_1$ represents a fluid inlet velocity that is directly measured, $\Delta m_1$ represents a mass of a drug or a medicament input per unit time t, $\rho_1$ represents a density of the input drug or medicament, $Vv_2$ represents an outlet fluid aspiration velocity that is directly measured, $\Delta m_2$ represents a mass of hematoma aspirated per unit time t, and $\rho_2$ represents a density of the aspirated hematoma;

the blood pressure can be measured by a sphygmomanometer;

the blood oxygen can be measured by an oximeter;

the heart rate can be measured by a heart rate monitor;

the intracranial pressure can be measured by an intracranial pressure monitor;

the hematoma location can be measured by a near-infrared measuring instrument; and the hematoma size cannot be directly measured, but rather in a manner of: measuring a hematoma location by a near-infrared probe, and then calculating a current hematoma size in combination with a mass of aspirated hematoma.

S104, inputting the real-time intraoperative data for hematoma aspiration into a second deep neural network that is constructed from an LSTM network and is preadapted by the most adapted clustering center, so as to determine a decision-making result of the hematoma aspiration protocol and a prediction result of the hematoma aspiration protocol intraoperatively, where the second deep neural network is configured to determine, based on the real-time intraoperative data for hematoma aspiration input into the network, a time series control protocol corresponding to a real-time hematoma aspiration process, and the time series control protocol includes protocol content of the hematoma aspiration protocol in a decision-making aspect and a prediction aspect.

It can be seen that according to the present application, the second deep neural network is specifically built using LSTM, that is Long Short-Term Memory (LSTM), and aims at prediction of time series data. This is to say, according to the present application, a real-time intraoperative hematoma aspiration protocol is taken as a time series data, and decision-making and prediction is carried out on this basis, so as to achieve a goal of performing real-time and high-accuracy control on the hematoma aspiration protocol.

Moreover, it should be noted that according to the present application, there is a matching mechanism between the second deep neural network and the clustering centers involved in the previous clustering processing. That is to say, different clustering centers are preadapted with different second deep neural networks, so that after the most adapted clustering center for the current situations of the patient is determined, the decision-making and prediction of the hematoma aspiration protocol, carried out in real time based on the second deep neural network preadapted by the most adapted clustering center, achieves better compatibility compared to that based on second deep neural networks preadapted by other clustering centers. This can promote better treatment and aspiration effects.

In specific operations, the first deep neural network and the second deep neural network can be combined into a multi-centered deep neural network. In this case, the first deep neural network, i.e., a first layer, can be understood as a multi-center clustering layer, and the second deep neural network, i.e., a second layer, can be understood as a multi-center real-time hematoma aspiration network.

In the intraoperative phase, since the second deep neural network is built for the most adapted center described previously, at the very beginning, hematoma aspiration protocols under different time series are analyzed by taking the previous initial hematoma aspiration protocol that is determined preoperatively or adopted at the beginning as a basis and combining with real-time intraoperative data for hematoma aspiration, and analysis results can be referred to as time series control protocols. In the time series control protocols, a hematoma aspiration protocol under a current time series is recommended for direct use, i.e., a decision-making result of the hematoma aspiration protocol, while hematoma aspiration protocols under subsequent time series are prediction results of the hematoma aspiration protocol. In actual situations, when the subsequent time series is reached, a new round of hematoma aspiration protocol under different time series can be analyzed in combination with new real-time intraoperative data for hematoma aspiration under the subsequent time series. In this way, the hematoma aspiration protocol can be continuously iterated and updated, and the adopted/applied hematoma aspiration protocol is continuously adjusted in real time, thereby achieving real-time and high-accuracy control effects on the hematoma aspiration protocol.

As an exemplary embodiment herein, the decision-making result of the hematoma aspiration protocol output by the second deep neural network specifically includes control amounts for both a fluid inlet amount and a fluid outlet amount by a micro metering pump.

The prediction result of the hematoma aspiration protocol output by the second deep neural network may specifically include two parts: a prediction result amount and a prediction decision amount, where the former, i.e., the prediction result amount, may include blood pressure, blood oxygen, a heart rate, intracranial pressure, a hematoma location, and a hematoma size, and the latter, i.e., the prediction decision amount, may include the fluid inlet amount and the fluid outlet amount.

Moreover, as an exemplary embodiment, the time series control protocol involved in the second deep neural network is represented as:

$$\{H_1, H_2, \ldots, H_t, \ldots, H_T\},$$

where $H_t$ is a control protocol (a hematoma aspiration protocol) at a moment t, T is a maximum value of t (i.e., t is a moment variable with a maximum value of T), and T corresponds to a total time (a total duration of a hematoma aspiration treatment), $$H_t = \{C_t, S_t, D_t\},$$

where $H_t$ includes a number of states at the moment t, including a control state $C_t$, a static state $S_t$, and a dynamic state $D_t$, specifically:

$C_t$ serves to control an action at a next moment, including a fluid inlet type, a fluid inlet velocity, and an aspiration velocity, $S_t$ is a descriptor value rather than a specific numerical value, serves as state monitoring, and includes a heart rate, blood pressure, and blood oxygen. For example, it may include specific descriptor values such as "normal", "slightly high", "slightly low", etc., $D_t$ is used to compare with an actual value to correct a control protocol $H_{t+1}$ at the next moment, including intracranial pressure, a hematoma size, and a hematoma location, the control protocol $H_{t+1}$ at the next moment is calculated by the following equation:

$$H_{t+1} = \delta[\omega_i(H_t, x_t) + b_i],$$

where $x_t$ is an actual state at the moment t, including intracranial pressure, a hematoma size, and a hematoma location that are actually measured, $\delta$, $\omega_i$, and $b_i$ are different network parameters (i.e., network parameters involved in an LSTM model itself) of the second deep neural network, and $x_t$ and $D_t$ are used to calculate a decision error and correct a decision value at the next moment by using the decision error so as to obtain an actual decision.

Figure 3:
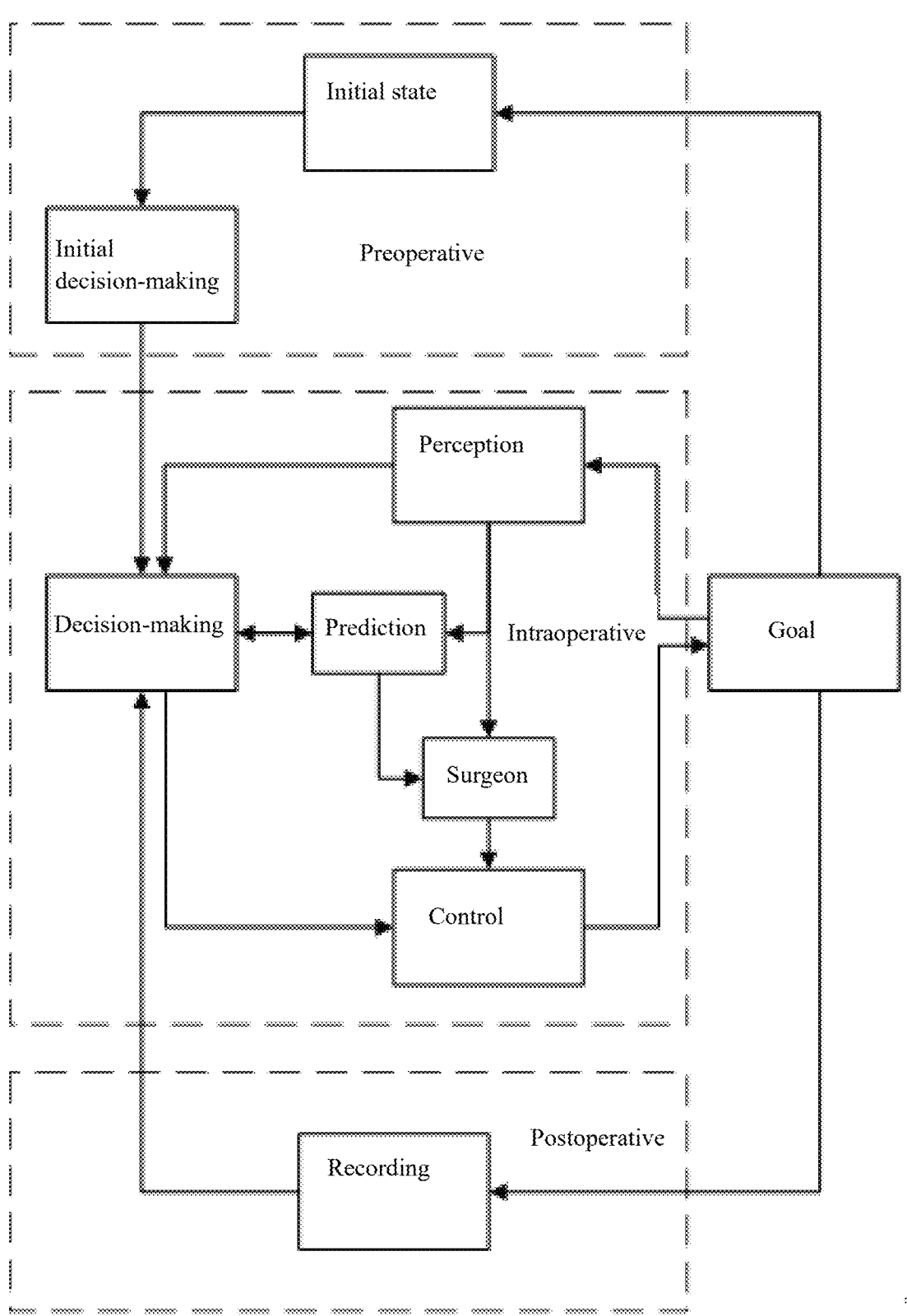
FIG. 3 is a scenario diagram of a working logic according to the solution of the present application.

For a more visual understanding, reference may also be made to FIG. 3 which illustrates a scenario diagram of a working logic according to the solution of the present application. Most of the above processing is processed by a decision-making module, $x_t$ (an actual state at the moment t) is obtained by a perception module, $C_t$ (a control state) is executed by a control module, and $D_t$ (a dynamic state) is predicted by a prediction module.

Moreover, the solution of the present application may be configured with a visualization mechanism, in order to show surgeons or medical staff the related situations during the hematoma aspiration treatment process assisted by the solution of the present application.

Correspondingly, the method according to the present application may further include:

displaying $H_t$, $C_t$, $S_t$, $D_t$, $x_t$, and the decision error through a visual interface.

It can be understood that a display screen involved in the visual interface can be either a structure of the system itself or external equipment (including specialized display equipment or other equipment with display screens).

On the basis of the visual interface, the solution of the present application can also introduce a human-machine fusion mechanism, so that the surgeons can make empirical judgments based on their work experience, in order to provide more suitable hematoma aspiration protocol control that is difficult for machines to learn in some special cases in the first time. Meanwhile, this mechanism also serves as a safeguard, providing an entry for manual intervention.

In this regard, as an exemplary embodiment, the method of the present application may further include:

receiving a control action $Y_t$ input by a decision-making participant (typically a surgeon), where $Y_t$ includes at least one of changing the fluid inlet type, adjusting the fluid inlet velocity, and adjusting the aspiration velocity; and executing $C_t$ and $Y_t$, and replacing $H_t$ with $H'_t$, where in $H'_t$, $C'_t = C_t + Y_t$, a remaining part is the same as $H_t$, and a calculation mode of $H_{t+1}$ is replaced with:

$$H_{t+1} = \delta[\omega_i(H'_t, x_t) + b_i],$$

$$H'_t = \{C'_t, S_t, D_t\},$$

$$C'_t = C_t + Y_t.$$

In this way, practically, a hematoma aspiration decision-making protocol adjusted by decision-making of the surgeon can guarantee better stability and safety in specific operations.

Moreover, in addition to the possibility of adjusting the decision-making based on the visual interface, an emergency stop control button can also be configured for the surgeons or medical staff. Through emergency stop control performed by the button, the occurrence of dangerous situations can be limited, and an alarm can be triggered simultaneously.

At the same time, it is readily appreciated that with the assistance of the decision-making system of the present application, the hematoma aspiration treatment process may also involve a data recording mechanism.

In this regard, a time interval can be set (e.g., 50 ms). At every time interval that passes, $D_t$ (a dynamic state) and $D_t$ (a dynamic state) are collected, $S_t$ (a static state) and a dynamic state $D_t$ (a dynamic state) are recorded. If the surgeon performs decision-making control, specific content of $Y_t$ (a control action) is recorded; and if the surgeon does not perform decision-making control, $Y_t$ is recorded as 0. A separate file is created for these data, which performs regular recording according to the time interval until the treatment is completed, and thus an entire process of the whole hematoma aspiration treatment is recorded.

Moreover, to achieve more convenient data recording effects and promote better data utilization effects, the present application can also be configured in the form of a decision-making matrix.

In this regard, eigenvalues obtained by numeralization of $H_t$, $C_t$, $S_t$, $D_t$, $x_t$, and $Y_t$ can also be standardized and recorded as a decision-making matrix represented as follows:

$$\begin{matrix} x_0 & x_1 & \dots & x_t \\ C_0 & C_1 & \dots & C_t \\ S_0 & S_1 & \dots & S_t \\ D_0 & D_1 & \dots & D_t \\ Y_0 & Y_1 & \dots & Y_t \end{matrix}$$

where in the decision-making matrix, each column represents all states and decision eigenvalues at a certain moment, and each row represents values of a certain feature at all moments.

Moreover, according to the present application, the second neural network (an LSTM network) mentioned previously can be optimized based on actual situations of a hematoma aspiration treatment/control protocol of a current patient, so as to achieve the effect of keeping iteration and update of the second neural network during actual use of the solution.

In this regard, it can also be combined with the processing setup of the decision-making matrix mentioned above. As an exemplary embodiment, the method of the present application may further include:

standardizing eigenvalues obtained by numeralization of $H_t$, $C_t$, $S_t$, $D_t$, $x_t$, and $Y_t$, and recording as a decision-making matrix represented as follows:

$$
\begin{matrix}
x_0 & x_1 & \dots & x_t \\
C_0 & C_1 & \dots & C_t \\
S_0 & S_1 & \dots & S_t \\
D_0 & D_1 & \cdots & D_t \\
Y_0 & Y_1 & \dots & Y_t
\end{matrix},
$$

where in the decision-making matrix, each column represents all states and decision eigenvalues at a certain moment, and each row represents values of a certain feature at all moments;

calculating an error between the decision-making matrix and an actual perceived value by the following equation:

$$
error = \| h_t - H_t \|,
$$

where $h_t$ is a decision output value of a decision-making model, and $H_t$ is an actual output value;

performing gradient optimization on $\delta$, $\omega_i$, and $b_i$ involved in the second deep neural network by using the error as a gradient direction, performing stepwise optimization on each moment (t-value), taking a finally optimized model as the second deep neural network preadapted by the most adapted clustering center, and categorizing information of a current patient in a point cluster of the most adapted clustering center, for subsequent clustering of the first deep neural network.

Moreover, it can be understood that according to the solution of the present application, the first deep neural network and the second deep neural network can be processed by a cloud server (including aspects such as storage, maintenance, and updating), so that remote data support in terms of models can be provided for different protocol deployment objects (which may involve objects at different granularities/levels such as hospitals, departments, or surgeons in actual situations), or even remote data support can be directly provided for the whole set of solution of the present application.

In this case, in the above embodiment, all parameters involved can be uploaded to the cloud server which carries out complex optimization on the second deep neural network by virtue of its powerful data processing capability, and finally optimized model parameters are then delivered for the protocol deployment objects of original uploaded data to perform model updating. In this way, in terms of local protocol deployment objects, individual differences in treatments of patients from different regions and with different characteristics can be improved, better pertinence and compatibility can be achieved, and effectiveness of hematoma aspiration treatments can be further improved; and in terms of the overall aspect, the effect of multi-center intelligent optimization (multi-center referring to multi-protocol deployment objects) can be achieved.

Whereas, if the second neural network is updated locally and autonomously, it is clear that model updating is performed locally and autonomously. In the case of similarly improving the individual differences in treatments of patients from local regions and with local characteristics, better autonomy can be achieved.

In general, it can be seen from the above solution content that according to the present application, aiming at a goal of assisting hematoma aspiration treatments, a two-layer deep neural network is constructed for processing of a hematoma aspiration protocol, and a perception-decision-making-control method based on a time series is thus realized, which overcomes unpredictability of results of hematoma aspiration processes existing in the prior art, provides direct and convenient information transmission for surgeons to make decisions, can effectively improve the accuracy of intracerebral hematoma aspiration treatment protocols, and provides digital, intelligent, and powerful support for clinical hematoma aspiration treatments.

The above is an introduction to a processing method of a hematoma aspiration decision-making system for intracerebral hemorrhage provided by the present application. To facilitate better implementation of the processing method of a hematoma aspiration decision-making system for intracerebral hemorrhage provided by the present application, the present application also provides a processing device of a hematoma aspiration decision-making system for intracerebral hemorrhage from the perspective of a functional module.

Figure 4:
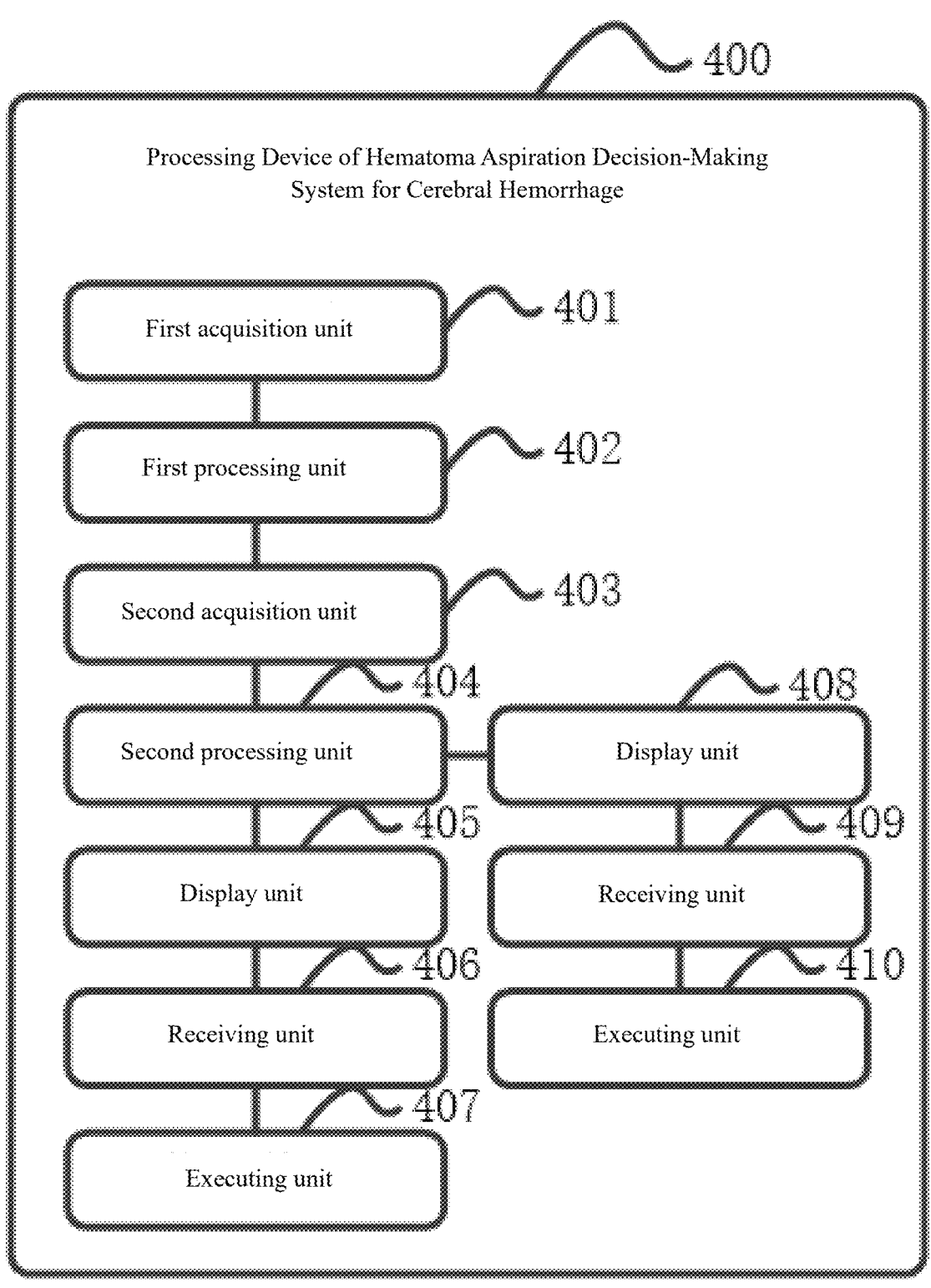
FIG. 4 is a schematic structural diagram of a processing device of a hematoma aspiration decision-making system for intracerebral hemorrhage according to the present application.

Referring to FIG. 4 which illustrates a schematic structural diagram of a processing device of a hematoma aspiration decision-making system for intracerebral hemorrhage according to the present application. In the present application, the processing device 400 of a hematoma aspiration decision-making system for intracerebral hemorrhage can specifically include the following structures:

a first acquisition unit 401, configured to acquire preoperative data for hematoma aspiration, where the preoperative data for hematoma aspiration involves a first indicator;

a first processing unit 402, configured to input the preoperative data for hematoma aspiration into a first deep neural network to determine an adapted initial hematoma aspiration protocol preoperatively, where the first deep neural network is configured to perform multi-center clustering on the preoperative data for hematoma aspiration input into the network and output a hematoma aspiration protocol preadapted by a most adapted clustering center;

a second acquisition unit 403, configured to acquire real-time intraoperative data for hematoma aspiration, where the real-time intraoperative data for hematoma aspiration involves a second indicator;

a second processing unit 404, configured to input the real-time intraoperative data for hematoma aspiration into a second deep neural network that is constructed from an LSTM network and is preadapted by the most adapted clustering center, so as to determine a decision-making result of the hematoma aspiration protocol and a prediction result of the hematoma aspiration protocol intraoperatively, where the second deep neural network is configured to determine, based on the real-time intraoperative data for hematoma aspiration input into the network, a time series control protocol corresponding to a real-time hematoma aspiration process, and the time series control protocol includes protocol content of the hematoma aspiration protocol in a decision-making aspect and a prediction aspect.

In an exemplary embodiment, the first indicator involved in the preoperative data for hematoma aspiration specifically includes:

an age, an NIHSS score, a medical history, blood pressure, blood oxygen, a heart rate, intracranial pressure, a hematoma location, a hematoma volume, a CT image, and an MRI image; and the second indicator involved in the intraoperative data for hematoma aspiration specifically includes:

an aspiration velocity, a fluid inlet velocity, blood pressure, blood oxygen, a heart rate, intracranial pressure, a hematoma location, and a hematoma size.

In an exemplary embodiment, the protocol content of the initial hematoma aspiration protocol includes:

a tolerance range of changes in intracranial pressure, a single aspiration duration, a hematoma state, whether other drug injections are needed, and a maximum aspiration velocity.

In another exemplary embodiment, the decision-making result of the hematoma aspiration protocol includes control amounts for both a fluid inlet amount and a fluid outlet amount by a micro metering pump;

the prediction result of the hematoma aspiration protocol includes a prediction result amount and a prediction decision amount, where the prediction result amount includes blood pressure, blood oxygen, a heart rate, intracranial pressure, a hematoma location, and a hematoma size, and the prediction decision amount includes the fluid inlet amount and the fluid outlet amount.

In another exemplary embodiment, for the second deep neural network, the time series control protocol is represented as:

$$\{H_1, H_2, \ldots, H_t, \ldots, H_T\},$$

where $H_t$ is a control protocol at a moment t, T is a maximum value of t, and T corresponds to a total time, $$H_t = \{C_t, S_t, D_t\},$$

where $H_t$ includes a number of states at the moment t, including a control state $C_t$, a static state $S_t$, and a dynamic state $D_t$, specifically:

$C_t$ serves to control an action at a next moment, including a fluid inlet type, a fluid inlet velocity, and an aspiration velocity, $S_t$ is a descriptor value rather than a specific numerical value, serves as state monitoring, and includes a heart rate, blood pressure, and blood oxygen, $D_t$ is used to compare with an actual value to correct a control protocol $H_{t+1}$ at the next moment, including intracranial pressure, a hematoma size, and a hematoma location, the control protocol $H_{t+1}$ at the next moment is calculated by the following equation:

$$H_{t+1} = \delta[\omega_i(H_t, x_t) + b_i],$$

where $x_t$ is an actual state at the moment t, including intracranial pressure, a hematoma size, and a hematoma location that are actually measured, $\delta$, $\omega_i$, and $b_i$ are different

16 network parameters of the second deep neural network, and $x_t$ and $D_t$ are used to calculate a decision error and correct a decision value at the next moment by using the decision error so as to obtain an actual decision.

In another exemplary embodiment, the device further includes:

a display unit 405, configured to display $H_t$, $C_t$, $S_t$, $D_t$, $x_t$, and the decision error through a visual interface;

a receiving unit 406, configured to receive a control action $Y_t$ input by a decision-making participant, where $Y_t$ includes at least one of changing the fluid inlet type, adjusting the fluid inlet velocity, and adjusting the aspiration velocity; and an executing unit 407, configured to execute $C_t$ and $Y_t$ and replace $H_t$ with $H'_t$, where in $H'_t$, $C'_t=C_t+Y_t$, a remaining part is the same as $H_t$, and a calculation mode of $H_{t+1}$ is replaced with:

$$H_{t+1} = \delta[\omega_i(H'_t, x_t) + b_i],$$

$$H'_t = \{C'_t, S_t, D_t\},$$

$$C'_t = C_t + Y_t.$$

In another exemplary embodiment, the device further includes:

a recording unit 408, configured to standardize eigenvalues obtained by numeralization of $H_t$, $C_t$, $S_t$, $D_t$, $x_t$, and $Y_t$ and record as a decision-making matrix represented as follows:

$$\begin{array}{cccc} x_0 & x_1 & \ldots & x_t \\ C_0 & C_1 & \ldots & C_t \\ S_0 & S_1 & \ldots & S_t \\ D_0 & D_1 & \ldots & D_t \\ Y_0 & Y_1 & \ldots & Y_t \end{array},$$

where in the decision-making matrix, each column represents all states and decision eigenvalues at a certain moment, and each row represents values of a certain feature at all moments;

a calculation unit 409, configured to calculate an error between the decision-making matrix and an actual perceived value by the following equation:

$$\text{error} = \|h_t - H_t\|,$$

where $h_t$ is a decision output value of a decision-making model, and $H_t$ is an actual output value;

an update unit 410, configured to perform gradient optimization on $\delta$, $\omega_i$, and $b_i$ involved in the second deep neural network by using the error as a gradient direction, perform stepwise optimization on each moment, take a finally optimized model as the second deep neural network preadapted by the most adapted clustering center, and categorize information of a current patient in a point cluster of the most adapted clustering center, for subsequent clustering of the first deep neural network.

Figure 5:
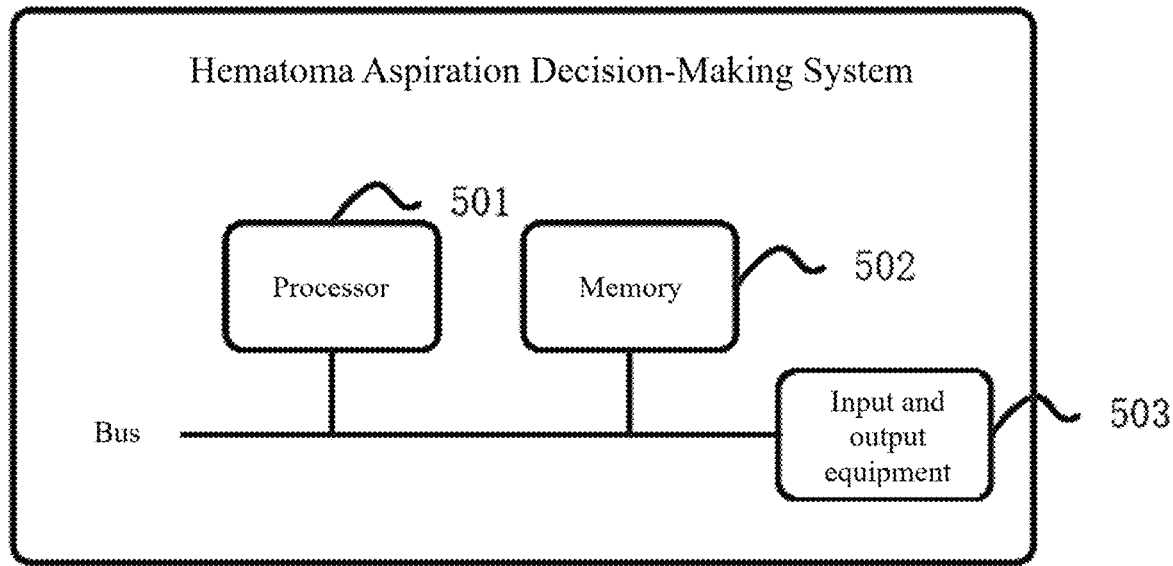
FIG. 5 is a schematic structural diagram of a hematoma aspiration decision-making system according to the present application.

The present application further provides a hematoma aspiration decision-making system from the perspective of a hardware structure, which is regarded as processing equipment. Referring to FIG. 5 which illustrates a schematic structural diagram of a hematoma aspiration decision-making system according to the present application. Specifically, the hematoma aspiration decision-making system of the present application may include a processor 501, a memory 502, and input and output equipment 503, where the processor 501 is used to implement steps of the processing method of a hematoma aspiration decision-making system for intracerebral hemorrhage in the embodiment corresponding to FIG. 1 when executing a computer program stored in the memory 502; alternatively, the processor 501 is used to implement functions of units in the embodiment corresponding to FIG. 4 when executing a computer program stored in the memory 502; and the memory 502 is used to store the computer program required for the processor 501 to execute the above processing method of a hematoma aspiration decision-making system for intracerebral hemorrhage in the embodiment corresponding to FIG. 1.

Exemplarily, the computer program may be partitioned into one or more modules/units, and the one or more modules/units are stored in the memory 502 and executed by the processor 501 to complete the present application. The one or more modules/units may be a series of computer program instruction segments capable of performing a particular function, and the instruction segments are used to describe a process of execution of the computer program in a computer device.

The hematoma aspiration decision-making system may include, but is not limited to, the processor 501, the memory 502, and the input and output equipment 503. It can be understood by those skilled in the art that the schematic diagram is only an example of the hematoma aspiration decision-making system and does not constitute a limitation of the hematoma aspiration decision-making system. It may include more or fewer components than those illustrated, or combinations of certain components, or different components. For example, the hematoma aspiration decision-making system may further include network access equipment, a bus, etc., and the processor 501, the memory 502, and the input and output equipment 503, etc. are connected through the bus.

The processor 501 may be a central processing unit (CPU), or it may be another general-purpose processor, a digital signal processor (DSP), an application specific integrated circuit (ASIC), a field-programmable gate array (FPGA), or other programmable logic devices, discrete gate or transistor logic devices, discrete hardware components, etc. The general-purpose processor may be a microprocessor, or the processor may also be any conventional processor, etc. The processor serves as a control center of the hematoma aspiration decision-making system, which connects all parts of the entire equipment by using various interfaces and circuits.

The memory 502 may be used to store a computer program and/or module, and the processor 501 implements various functions of the computer device by running or executing the computer program and/or module stored in the memory 502 and by calling data stored in the memory 502. The memory 502 may primarily include a program storage region and a data storage region, where the program storage region may store an operating system, application programs required for at least one function, etc.; and the data storage region may store data created based on use of the hematoma aspiration decision-making system, etc. Moreover, the memory may include a high-speed random access memory, and may also include a non-volatile memory, such as a hard disk, a memory, a plug-in hard disk, a smart media card (SMC), a secure digital (SD) card, a flash card, at least one disk storage device, a flash device, or other volatile solid-state storage device.

The processor 501, when used to execute the computer program stored in the memory 502, may specifically implement the following functions:

acquiring preoperative data for hematoma aspiration, where the preoperative data for hematoma aspiration involves a first indicator;

inputting the preoperative data for hematoma aspiration into a first deep neural network to determine an adapted initial hematoma aspiration protocol preoperatively, where the first deep neural network is configured to perform multi-center clustering on the preoperative data for hematoma aspiration input into the network and output a hematoma aspiration protocol preadapted by a most adapted clustering center;

acquiring real-time intraoperative data for hematoma aspiration, where the real-time intraoperative data for hematoma aspiration involves a second indicator;

inputting the real-time intraoperative data for hematoma aspiration into a second deep neural network that is constructed from an LSTM network and is preadapted by the most adapted clustering center, so as to determine a decision-making result of the hematoma aspiration protocol and a prediction result of the hematoma aspiration protocol intraoperatively, where the second deep neural network is configured to determine, based on the real-time intraoperative data for hematoma aspiration input into the network, a time series control protocol corresponding to a real-time hematoma aspiration process, and the time series control protocol includes protocol content of the hematoma aspiration protocol in a decision-making aspect and a prediction aspect.

It can be clearly understood by those skilled in the art that for the convenience and concision of the description, specific working processes of the processing device of a hematoma aspiration decision-making system for intracerebral hemorrhage, the hematoma aspiration decision-making system, and corresponding units thereof described above can refer to the illustration of the processing method of a hematoma aspiration decision-making system for intracerebral hemorrhage in the embodiment corresponding to FIG. 1, and will not be specifically detailed herein.

Those of ordinary skill in the art can understand that all or part of steps in various methods of the above embodiments can be completed by instructions or by controlling related hardware through the instructions, which can be stored in a computer-readable storage medium and loaded and executed by a processor.

In this regard, the present application provides a computer-readable storage medium, having a plurality of instructions stored therein, where the instructions can be loaded by a processor to execute steps of the processing method of a hematoma aspiration decision-making system for intracerebral hemorrhage in the embodiment corresponding to FIG. 1. Specific operations can refer to the illustration of the processing method of a hematoma aspiration decision-making system for intracerebral hemorrhage in the embodiment corresponding to FIG. 1, and will not be detailed herein.

The computer-readable storage medium may include: a read only memory (ROM), a random access memory (RAM), a magnetic disk or an optical disk and the like.

Since the instructions stored in the computer-readable storage medium can execute the steps of the processing method of a hematoma aspiration decision-making system for intracerebral hemorrhage in the embodiment corresponding to FIG. 1 of the present application, it is possible to achieve beneficial effects that can be achieved by the processing method of a hematoma aspiration decision-making system for intracerebral hemorrhage in the embodiment corresponding to FIG. 1 of the present application. Specific operations are shown in the previous description, and will not be detailed herein.

The processing method and device of a hematoma aspiration decision-making system for intracerebral hemorrhage, the hematoma aspiration decision-making system, and the computer-readable storage medium provided by the present application are introduced in detail above. Specific examples are applied herein to illustrate the principles and implementations of the present application, and the illustrations of the above embodiments are only used to assist in the understanding of the method of the present application and core ideas thereof. Meanwhile, those skilled in the art can understand that there may be changes in the specific implementations and the scope of application based on the ideas of the present application. In summary, the content of this specification should not be understood as a limitation of the present application.

The invention claimed is:

1. A processing method of a hematoma aspiration decision-making system implemented in and physically controlling a hematoma aspiration apparatus comprising a micro flowmeter, a gravimeter, a sphygmomanometer, an oximeter, a heart rate monitor, an intracranial pressure monitor, a near-infrared measuring instrument, a near-infrared probe and a micro metering pump during an intracerebral hemorrhage surgery, wherein the method comprises:

acquiring preoperative data for hematoma aspiration, wherein the preoperative data for hematoma aspiration involves a first indicator;

inputting the preoperative data for hematoma aspiration into a first deep neural network to determine an adapted initial hematoma aspiration protocol preoperatively, wherein the first deep neural network is configured to perform multi-center clustering on the preoperative data for hematoma aspiration input into the network and output a hematoma aspiration protocol preadapted by a most adapted clustering center;

acquiring real-time intraoperative data for hematoma aspiration through the hematoma aspiration apparatus, wherein the real-time intraoperative data for hematoma aspiration involves a second indicator, the second indicator comprises an aspiration velocity, a fluid inlet velocity, blood pressure, blood oxygen, a heart rate, intracranial pressure, a hematoma location, and a hematoma size;

selecting, from a plurality of pre-trained Long Short-Term Memory (LSTM) networks, a specific LSTM network that is preadapted by and corresponds to the most adapted clustering center determined by the first deep neural network;

inputting the real-time intraoperative data for hematoma aspiration into a second deep neural network distinct from the first deep neural network, wherein the second deep neural network corresponds to the selected specific LSTM network, so as to determine a decision-making result of the hematoma aspiration protocol and a prediction result of the hematoma aspiration protocol intraoperatively, wherein the second deep neural network is configured to determine, based on the real-time intraoperative data for hematoma aspiration input into the network, a time series control protocol corresponding to a real-time hematoma aspiration process, and the time series control protocol comprises protocol content of the hematoma aspiration protocol in a decision-making aspect and a prediction aspect, wherein the decision-making result comprises control amounts for a fluid inlet amount and a fluid outlet amount by the micro metering pump, and the prediction result comprises a prediction result amount and a prediction decision amount, wherein the prediction result amount comprises blood pressure, blood oxygen, a heart rate, intracranial pressure, a hematoma location, and a hematoma size, and the prediction decision amount comprises the fluid inlet amount and the fluid outlet amount; and generating, based on the decision-making result, one or more control signals that directly drive the micro metering pump of the hematoma aspiration apparatus to dynamically and physically control a fluid inlet amount through the fluid inlet channel and a fluid outlet amount through the fluid outlet channel during the intracerebral hemorrhage surgery, wherein the micro flowmeter provides instantaneous flow-rate feedback, the gravimeter measures mass change to correct the flow-rate measurement; wherein the method implements a real-time closed-loop control of the hematoma aspiration apparatus by iteratively updating the hematoma aspiration protocol based on newly acquired intraoperative data at each subsequent moment, thereby achieving real-time and high-accuracy control of the hematoma aspiration process;

for the second deep neural network, the time series control protocol being represented as:

$$\{H_1, H_2, \dots, H_t, \dots, H_T\},$$

$H_t$ is a control protocol at a moment t, T is a maximum value of t, and T corresponds to a total time, $$H_t = \{C_t, S_t, D_t\},$$

wherein
$H_t$ comprises a number of states at the moment t, comprising a control state $C_t$, a static state $S_t$, and a dynamic state $D_t$, specifically:
$C_t$ serves to control an action at a next moment of the hematoma aspiration device, comprising a fluid inlet type, a fluid inlet velocity, and an aspiration velocity,
$S_t$ is a descriptor value rather than a specific numerical value, serves as state monitoring, and comprises a heart rate, blood pressure, and blood oxygen,
$D_t$ is used to compare with an actual value to correct a control protocol $H_{t+1}$ at the next moment, comprising intracranial pressure, a hematoma size, and a hematoma location,
the control protocol $H_{t+1}$ at the next moment is calculated by the following equation:

$$H_{t+1} = \delta[\omega_i(H_t, x_t) + b_i],$$

wherein $X_t$ is an actual state at the moment t, comprising intracranial pressure, a hematoma size, and a hematoma location that are actually measured, δ, $\omega_i$, and $b_i$ are different network parameters of the second deep neural network, and $x_t$, and $D_t$ are used to calculate a decision error and correct a decision value at the next moment by using the decision error so as to obtain an actual decision.

2. The method according to claim 1, wherein the first indicator involved in the preoperative data for hematoma aspiration specifically comprises:

an age, an NIHSS score, a medical history, blood pressure, blood oxygen, a heart rate, intracranial pressure, a hematoma location, a hematoma volume, a CT image, and an MRI image; and the second indicator involved in the intraoperative data for hematoma aspiration specifically comprises:

an aspiration velocity, a fluid inlet velocity, blood pressure, blood oxygen, a heart rate, intracranial pressure, a hematoma location, and a hematoma size.

3. The method according to claim 1, wherein the protocol content of the initial hematoma aspiration protocol comprises:

a tolerance range of changes in intracranial pressure, a single aspiration duration, a hematoma state, whether other drug injections are needed, and a maximum aspiration velocity.

4. The method according to claim 1, wherein the method further comprises:

displaying $H_t$, $C_t$, $S_t$, $D_t$, $X_t$, and the decision error through a visual interface;

receiving a control action $Y_t$ input by a decision-making participant, wherein $Y_t$ comprises at least one of changing the fluid inlet type, adjusting the fluid inlet velocity, and adjusting the aspiration velocity; and executing $C_t$ and $Y_t$, and replacing $H_t$ with $H'_t$, wherein in $H'_t$, $C'_t = C_t + Y_t$, a remaining part is the same as $H_t$, and a calculation mode of $H_{t+1}$ is replaced with:

$$H_{t+1} = \delta[\omega_i(H'_t, x_t) + b_i],$$

$$H'_t = \{C'_t, S_t, D_t\},$$

$$C'_t = C_t + Y_t.$$

5. The method according to claim 4, wherein the method further comprises:

standardizing eigenvalues obtained by numeralization of $H_t$, $C_t$, $S_t$, $D_t$, $X_t$, and $Y_t$, and recording as a decision-making matrix represented as follows:

$$\begin{matrix} x_0 & x_1 & \dots & x_t \\ C_0 & C_1 & \dots & C_t \\ S_0 & S_1 & \dots & S_t \\ D_0 & D_1 & \dots & D_t \\ Y_0 & Y_1 & \dots & Y_t \end{matrix},$$

in the decision-making matrix, each column represents all states and decision eigenvalues at a certain moment, and each row represents values of a certain feature at all moments;

calculating an error between the decision-making matrix and an actual perceived value by the following equation:

$$\text{error} = \|h_t - H_t\|,$$

$h_t$ is a decision output value of a decision-making model, and $H_t$ is an actual output value;

performing gradient optimization on δ, $\omega_i$, and $b_i$ involved in the second deep neural network by using the error as a gradient direction, performing stepwise optimization on each moment, taking a finally optimized model as the second deep neural network preadapted by the most adapted clustering center, and categorizing information of a current patient in a point cluster of the most adapted clustering center, for subsequent clustering of the first deep neural network.

6. A processing device of a hematoma aspiration decision-making system for intracerebral hemorrhage, wherein the device comprises:

a processor; and a memory storing instructions that, when executed by the processor, cause the processing device to perform operations comprising:

acquiring preoperative data for hematoma aspiration from one or more medical sensors or databases, wherein the preoperative data for hematoma aspiration involves a first indicator;

inputting the preoperative data for hematoma aspiration into a first deep neural network to determine an adapted initial hematoma aspiration protocol preoperatively, wherein the first deep neural network is configured to perform multi-center clustering on the preoperative data for hematoma aspiration input into the network and output a hematoma aspiration protocol preadapted by a most adapted clustering center;

acquiring real-time intraoperative data for hematoma aspiration through the hematoma aspiration apparatus, wherein the real-time intraoperative data for hematoma aspiration involves a second indicator, the second indicator comprises an aspiration velocity, a fluid inlet velocity, blood pressure, blood oxygen, a heart rate, intracranial pressure, a hematoma location, and a hematoma size;

selecting, from a plurality of pre-trained Long Short-Term Memory (LSTM) networks, a specific LSTM network that is preadapted by and corresponds to the most adapted clustering center determined by the first deep neural network;

inputting the real-time intraoperative data for hematoma aspiration into the a second deep neural network distinct from the first deep neural network, wherein the second deep neural network corresponds to the selected specific LSTM network, so as to determine a decision-making result of the hematoma aspiration protocol and a prediction result of the hematoma aspiration protocol intraoperatively, wherein the second deep neural network is configured to determine, based on the real-time intraoperative data for hematoma aspiration input into the network, a time series control protocol corresponding to a real-time hematoma aspiration process, and the time series control protocol comprises protocol content of the hematoma aspiration protocol in a decision-making aspect and a prediction aspect, wherein the decision-making result comprises control amounts for a fluid inlet amount and a fluid outlet amount by a micro metering pump, and the prediction result comprises a prediction result amount and a prediction decision amount, wherein the prediction result amount comprises blood pressure, blood oxygen, a heart rate, intracranial pressure, a hematoma location, and a hematoma size, and the prediction decision amount comprises the fluid inlet amount and the fluid outlet amount; and generating, based on the decision-making result, one or more control signals that directly drive the micro metering pump of a hematoma aspiration apparatus to dynamically and physically control a fluid inlet amount through the fluid inlet channel and a fluid outlet amount through the fluid outlet channel during an intracerebral hemorrhage surgery, wherein the micro flowmeter provides instantaneous flow-rate feedback, the gravimeter measures mass change to correct the flow-rate measurement; wherein the method implements a real-time closed-loop control of the hematoma aspiration apparatus by iteratively updating the hematoma aspiration protocol based on newly acquired intraoperative data at each subsequent moment, thereby achieving real-time and high-accuracy control of the hematoma aspiration process;

wherein for the second deep neural network, the time series control protocol is represented as:

$$\{H_1, H_2, \ldots, H_t, \ldots, H_T\},$$

wherein $H_t$ is a control protocol at a moment t, T is a maximum value of t, and T corresponds to a total time, $$H_t = \{C_t, S_t, D_t\},$$

wherein $H_t$ comprises a number of states at the moment t, comprising a control state $C_t$, a static state $S_t$, and a dynamic state $D_t$, specifically:

$C_t$ serves to control an action at a next moment, comprising a fluid inlet type, a fluid inlet velocity, and an aspiration velocity, $S_t$ is a descriptor value rather than a specific numerical value, serves as state monitoring, and comprises a heart rate, blood pressure, and blood oxygen, $D_t$ is used to compare with an actual value to correct a control protocol $H_{t+1}$ at the next moment, comprising intracranial pressure, a hematoma size, and a hematoma location, the control protocol $H_{t+1}$ at the next moment is calculated by the following equation:

$$H_{t+1} = \delta[\omega_i(H_t, x_t) + b_i],$$

wherein $X_t$ is an actual state at the moment t, comprising intracranial pressure, a hematoma size, and a hematoma location that are actually measured, $\delta$, $\omega_i$, and $b_i$ are different network parameters of the second deep neural network, and $x_t$ and $D_t$ are used to calculate a decision error and correct a decision value at the next moment by using the decision error so as to obtain an actual decision.

7. A hematoma aspiration decision-making system, comprising a processor and a memory, wherein the memory has a computer program stored therein, and the processor, when calling the computer program in the memory, executes the method according to claim 1.

8. A non-transitory computer-readable storage medium, wherein the computer-readable storage medium stores a plurality of instructions; and the instructions are suitable for being loaded by a processor to execute the method according to claim 1.

* * * * *